(12) United States Patent
van Heerde et al.

(10) Patent No.: US 9,856,510 B2
(45) Date of Patent: Jan. 2, 2018

(54) CHEMILUMINESCENCE-BASED HAEMOSTASIS ASSAY

(75) Inventors: Waander Laurens van Heerde, Nijmegen (NL); Richard Hendrik Blaauw, The Netherlands (NL)

(73) Assignees: Stichting Katholieke Universiteit, Nijmegen (NL); Chiralix B.V., Nijmegen (NL)

( * ) Notice: Subject to any disclaimer, the term of this patent is extended or adjusted under 35 U.S.C. 154(b) by 88 days.

(21) Appl. No.: 13/993,992

(22) PCT Filed: Dec. 14, 2011

(86) PCT No.: PCT/NL2011/050850
§ 371 (c)(1),
(2), (4) Date: Aug. 16, 2013

(87) PCT Pub. No.: WO2012/096566
PCT Pub. Date: Jul. 19, 2012

(65) Prior Publication Data
US 2013/0337480 A1 Dec. 19, 2013

Related U.S. Application Data

(60) Provisional application No. 61/422,751, filed on Dec. 14, 2010.

(30) Foreign Application Priority Data

Dec. 14, 2010 (NL) ...................................... 2005858

(51) Int. Cl.
C12Q 1/66 (2006.01)
C12Q 1/37 (2006.01)
C12Q 1/56 (2006.01)

(52) U.S. Cl.
CPC ................. *C12Q 1/37* (2013.01); *C12Q 1/56* (2013.01); *C12Q 1/66* (2013.01); *G01N 2333/745* (2013.01)

(58) Field of Classification Search
None
See application file for complete search history.

(56) References Cited

U.S. PATENT DOCUMENTS

| | | | | |
|---|---|---|---|---|
| 4,409,140 A * | 10/1983 | Smith | .................. | C07D 311/16 435/24 |
| 4,640,893 A | 2/1987 | Mangel et al. | | |
| 5,035,999 A | 7/1991 | Geiger et al. | | |
| 2003/0186345 A1* | 10/2003 | Hortin | ...................... | C12Q 1/37 435/23 |
| 2005/0228020 A1* | 10/2005 | Miyamoto et al. | ........... | 514/319 |
| 2006/0073529 A1* | 4/2006 | Contag et al. | ............... | 435/7.23 |
| 2006/0217317 A1* | 9/2006 | Denmeade | ....... | A61K 47/48238 514/1.3 |
| 2009/0137790 A1* | 5/2009 | Enya | .......................... | 536/25.33 |
| 2011/0105408 A1* | 5/2011 | Agrez | .............. | A61K 47/48215 514/19.3 |

FOREIGN PATENT DOCUMENTS

| WO | WO 9322453 A1 * | 11/1993 |
|---|---|---|
| WO | WO-2006072602 A1 | 7/2006 |
| WO | WO-2010006605 A2 | 1/2010 |

OTHER PUBLICATIONS

Dragulescu-Andrasi et al. Bioconj. Chem. (2009) 20: 1660-1666, published online Jul. 31, 2009.*
Boyer Chem. Rev. (1980) 80: 495-561.*
R. A. Moravec et al. "Cell-based proteasome assays for all three proteasome activities in a homogeneous format," Analytical Biochemistry 387, 294-302, (2009).
N. Crosby et al. "Custom Enzyme Substrates for Luciferase-Based Assays," Cell notes, Issue 8, pp. 9-11, (2007).
International Search Report issued in PCT/NL2011/050850, dated May 8, 2012.
International Search Report issued in Netherlands Patent Application No. 2005858, dated Jul. 21, 2011. (Dutch).
I. Schousboe, "Factor XIIa activation of plasminogen is enhanced by contact activating surfaces and $Zn^{2+}$," Blood Coagulation and Fibrinolysis, vol. 8, 1997, 97-104.
G. Meroni et al., "D-Luciferin, derivatives and analogues; synthesis and in vitro/in vivo luciferase-catalyzed bioluminescent activity," Special Issue Reviews and Accounts ARKIVOC 2009 (i) 265-288.

* cited by examiner

*Primary Examiner* — Susan Hanley
(74) *Attorney, Agent, or Firm* — Locke Lord LLP; Nicholas J. DiCeglie, Jr.

(57) ABSTRACT

The present invention relates to a method for in vitro determining generation of a haemostatis factor such as thrombin and/or plasmin in a test sample using a chemiluminescent substrate specific for said blood clotting factor. Upon cleavage of the substrate, a luminescent signal is generated via aminoluceferin with the aid of a luciferase. The invention also relates to a kit for in vitro determining generation of a haemostasis factor in a test sample, and to novel chemiluminescent substrates for the determination of thrombin and plasmin.

20 Claims, 3 Drawing Sheets

CHEMILUMINESCENCE-BASED HAEMOSTASIS ASSAY

CROSS REFERENCE TO RELATED APPLICATIONS

This application is a 371 U.S. National Phase Application of PCT/NL2011/050850 filed Dec. 14, 2011, which claims priority to Netherlands Patent Application No. 2005858, filed Dec. 14, 2010, and U.S. Provisional Patent Application No. 61/422,751, filed Dec. 14, 2010, the disclosures of each of which are expressly incorporated herein by reference in their entireties.

FIELD OF THE INVENTION

The present invention is in the field of medicine, in particular in the field of blood coagulation. More specifically, the invention relates to a novel method for direct measuring the generation of haemostasis factors using a substrate that produces an optical signal upon activation by a blood clotting and/or fibrinolytic factor of interest. 'Direct' in the previous sentence means that there is no need to transform or adapt the generated signal.

BACKGROUND OF THE INVENTION

The haemostatic balance is dependent on interactions between platelets, vessel-wall coagulation and fibrinolysis. Upon vessel wall injury platelets adhere to the subendothelium and form aggregates. Next, coagulation is initiated ultimately resulting in the production of fibrin fibers that stabilize the platelet plug. All these steps are important to form a stable blood clot that is resistant against the rheological forces of the blood flow. Thrombin is a key player in these processes as it is responsible for a whole concert of reactions, for instance it solidifies the blood by formation of fibrin, activates platelets, activates positive feedback mechanisms and interacts with the endothelial receptors to start negative feedback mechanisms. Activated platelets, in their turn catalyze thrombin formation. Thrombin has a short half-life, approximately a few minutes, which is caused by the binding of thrombin inhibitors like antithrombin. Antithrombins also act as regulatory proteins, which can inactivate the first traces of thrombin before they can augment thrombin generation by positive feedback reactions. This prevents systemic clot formation. Fibrinolysis on its turn solubilizes the fibrin containing platelet plug. Disequilibrium of this haemostatic balance in one or more compartments (vessel wall, blood cells, coagulation and fibrinolysis) may result in a thrombotic response or hemorrhagic phenotype which even can be life threatening.

When abnormalities of the haemostatic system occur, it is essential to diagnose, monitor, and manage the patient in order to optimize therapeutic intervention.

Known haemostasis assays involve end-point assays, which detect the clotting time of blood plasma (clotting assays) or real-time clot-lysis by means of turbidimetry (fibrinolysis assays). Although performed routinely, the currently available coagulation assays have inherent limitations that make them potentially unreliable as tools for monitoring increased coagulation. Moreover, there is not always a good correlation between the results of coagulation tests and the prevention of postoperative hemorrhage or recurrent thrombosis (Hemker et al. Curr. Opin. in Hematology 2004, 11:170-175).

Most of the limitations relate to the fact that these are end-point tests that measure the time of clot formation in vitro and require the addition of exogenous reagents (such as tissue factor, kaolin and $Ca^{2+}$ ions to replenish those bound by an anticoagulant), and thus do not necessarily reflect the patient's thrombotic potential (clotting potential).

As compared to the tests described above, EP 420 332 discloses an improved thrombin generation assay. In this assay not only information is gathered about the clotting of plasma but also about the total thrombin generation after clot formation. These assays were first performed with chromogenic substrates and later on with fluorogenic substrates. Furthermore, several thrombin generation assays with platelet-poor and platelet-rich plasma are disclosed.

The chromophores (e.g. p-nitro-anilin [p-NA]) used in chromogenic assays are typically assessed using a wavelength of 405 nm. An important drawback of chromogenic substrates is that both fibrin and platelets in aqueous solutions interfere with the assessment of chromogenic substrates at 405 nm, and that the measurement as such is unreliable. Therefore, the use of fluorogenic substrates is nowadays more popular. Fluorogenic substrates are analogous to chromogenic substrates. The difference is that upon enzymatic action the substrates release a group which can be determined with high sensitivity using a fluorometer. Fluorometric assessment of thrombin generation further has the advantage that fibrin or platelets do not interfere with the analysis.

Furthermore, the use of multiple fluorogenic substrates with different characteristics allow the detection of several products in one sample as described in WO 2006/072602. The use of fluorogenic substrates also has significant disadvantages: the standard laboratory equipment used for analysis of the coagulation system does not support fluorometric analysis. Thus the analysis requires additional instrumentation (fluorometer). In addition the trend of the last decade has been to implement all coagulation tests wherever possible on one analyzer in order to simplify the testing procedure and minimize labor costs. The use of a separate instrument for measuring thrombin generation significantly reduces its applicability as a routine method. Further, the fluorescent signal has the drawback of not being linear with product concentration. A need exists for a new assay for measuring thrombin generation and generation of other blood clotting factors that does not have the above indicated drawbacks, that is simpler and can measure the generation of blood clotting and fibrinolytic factors such as thrombin and plasmin in a direct manner, preferably in a linear mode. It is an object of the present invention to provide such assay.

SUMMARY OF THE INVENTION

The present invention provides a method for in vitro determining generation of a haemostasis factor, preferably a blood clotting and/or a fibrinolytic factor, in a test sample comprising determining the amount of said haemostasis factor, e.g., thrombin or plasmin, generated using a chemiluminescent substrate specific for said haemostasis factor. Said chemiluminescent substrate used in a method according to the invention is typically a chemiluminogenic substrate from which a chemiluminescent molecule is liberated by a haemostasis factor and is subsequently converted to produce a detectable light quant.

The incorporation of a chemiluminescent molecule in a substrate for thrombin has been suggested in WO 93/22453. However, WO 93/22453 does not disclose any suitable chemiluminescent substrates. Moreover, the methodology for determining thrombin generation disclosed in WO 93/22453 is exclusively geared towards fluorescence based assays.

In order to provide an assay relying on the use of chemiluminescent substrates, several difficulties had to be resolved, including, not in the last place, the actual development of suitable chemiluminescent substrates that are cleaved efficiently and with sufficient specificity by haemostasis factors. At the same time, it would have been presumed by those skilled in the art that chemiluminescence based assays would in fact become too complex and, in fact, unfeasible. The assay for e.g. thrombin or plasmin generation, which in itself is already complex, becomes even more complex, as another reaction is added into the equation. Moreover, chemiluminescence has always been presumed difficult to measure in the blood.

In a first aspect, the present invention relates to a method for in vitro determining generation of a haemostasis factor in a test sample comprising determining the amount of said haemostasis factor, e.g. thrombin and/or plasmin, generated using a chemiluminescent substrate specific for said haemostasis factor, wherein preferably a chemiluminescent molecule is liberated by a haemostasis factor which is subsequently converted to produce a detectable light quant.

In a further aspect, the present invention is concerned with a kit for in vitro determining generation of a haemostasis factor in a test sample, comprising a first container holding a chemiluminescent substrate specific for said haemostasis factor, and one, two, three or more additional containers each holding a distinct reagent selected from the group consisting of luciferase, adenosine-5'-triphosphate (ATP), an $Mg^{2+}$ source and one or more trigger molecules for inducing generation of said haemostasis factor. Preferably the trigger molecule is for inducing generation of a haemostasis factor selected from the group consisting of a blood clotting factor and a fibrinolytic factor. Preferably the trigger molecule is for inducing generation of a haemostasis factor selected from the group consisting of thrombin and plasmin.

In a further aspect, the present invention is concerned with a kit for in vitro determining thrombin generation in a test sample, comprising a first container holding a chemiluminescent thrombin substrate, and one, two, three or more additional containers, each holding a distinct reagent selected from the group consisting of luciferase, ATP, an $Mg^{2+}$ source and one or more trigger molecules for inducing thrombin generation.

In another aspect, the present invention pertains to a kit for in vitro determining plasmin generation in a test sample, comprising a first container holding a chemiluminescent plasmin substrate, and one, two, three or more additional containers each container comprising a distinct reagent selected from the group consisting of luciferase, ATP, an $Mg^{2+}$ source and one or more trigger molecules for inducing plasmin generation In a further aspect, the invention deals with novel chemiluminescent thrombin substrates, in particular RO—$[CH_2CH_2O]_n$-(Sp)-Gly-Gly-Arg-aminoluciferin and RO—$[CH_2CH_2O]_n$-(Sp)-beta-Ala-Gly-Arg-aminoluciferin, or a salt thereof, wherein R is H or $C_1$-$C_6$ alkyl, n is an integer in the range of 0-10, Sp is an optional spacer moiety. Preferably n is in the range from 1-8, more preferably in the range from 2-5. In one embodiment R is $CH_3$. In one embodiment a spacer moiety is present. A preferred spacer moiety is $[CH_2]_m C=O$, wherein m is an integer in the range from 1-6, preferably 1-4. A preferred spacer moiety is $CH_2C=O$. Preferred chemiluminescent thrombin substrates that can suitably be used in accordance with the present invention are $CH_3O(CH_2CH_2O)_2$-acetyl-Gly-Gly-Arg-aminoluciferin or a salt thereof (formula 1) and $CH_3O(CH_2CH_2O)_2$-acetyl-beta-Ala-Gly-Arg-aminoluciferin (formula 2) or a salt thereof. In one embodiment the substrate is a TFA (trifluoroacetic acid) salt. These novel chemiluminescent thrombin substrates can be represented by the following structure formulas:

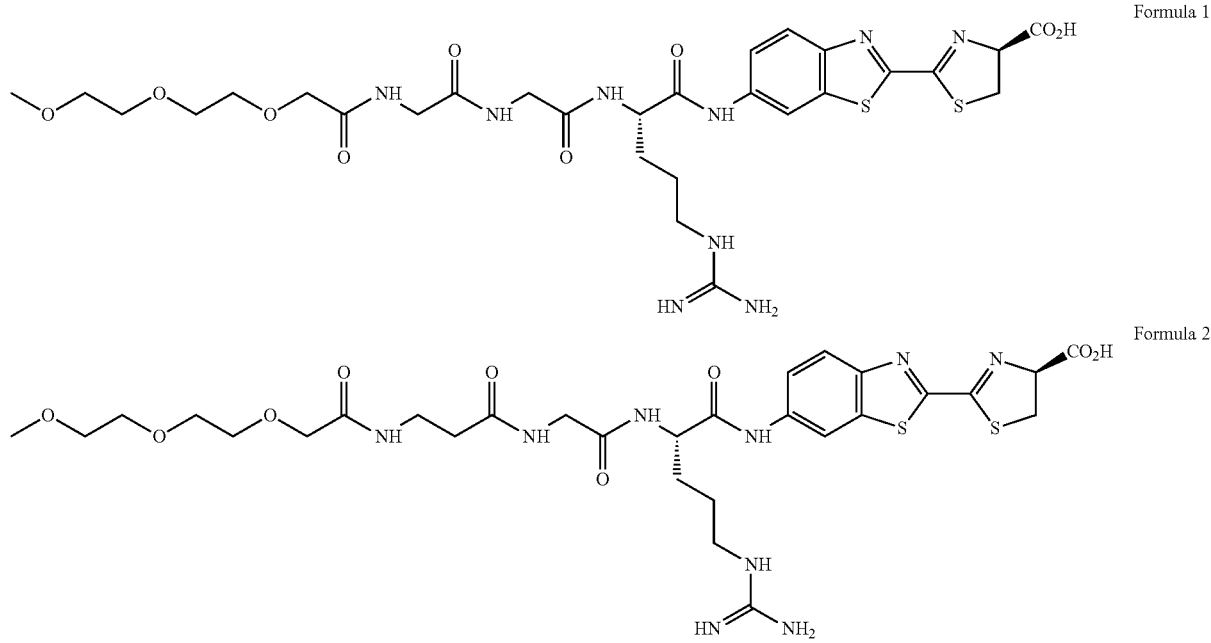

In a further aspect, the invention deals with a novel chemiluminescent plasmin substrate that can suitably be used in accordance with the present invention, in particular pyroGlu-Phe-Lys-aminoluciferin, or a salt thereof (formula 3). In one embodiment the substrate is a TFA (trifluoroacetic acid) salt. This novel chemiluminescent plasmin substrate can be represented by the following structure formula:

Formula 3

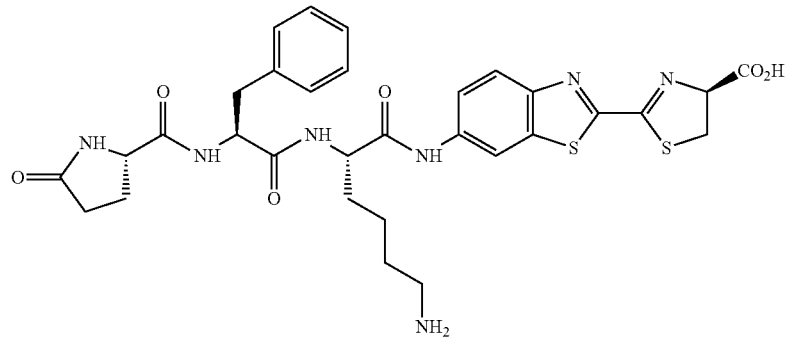

Preferred chemiluminescent substrates according to the invention are:

B—X-Arg-NH—Y, X-Arg-NH—Y, B—X-Lys-NH—Y or X-Lys-NH—Y, wherein B is an amino-terminal protecting group, preferably Fmoc; Cbz; t-Boc; acetyl; $PEG_n$, $PEG_n$-acetyl, wherein n is an integer, preferably in the range of 1-5, and their PEG(methyl)ether derivates; wherein Y is a chemiluminescent reporter molecule linked to the peptide by a hydrolyzable amide bond, preferably Y is aminoluciferin; wherein X may be any amino acid sequence, dipeptide, tripeptide, or the like and may or may not include a spacer molecule, wherein X preferably is beta-Ala-Gly or pyroGlu-Phe;

pyroGlu-Phe-Lys-aminoluciferin;

$CH_3O(CH_2CH_2O)_n$-acetyl-Gly-Gly-Arg-aminoluciferin, wherein n is 0, 1, 2, 3, or 4, preferably 2 or 4, more preferably 2;

$CH_3O(CH_2CH_2O)_n$-acetyl-beta-Ala-Gly-Arg-aminoluciferin, wherein n is 0, 1, 2, 3, or 4, preferably 2 or 4, more preferably 4;

a salt of the substrates here above, preferably the TFA salt.

DETAILED DESCRIPTION OF EMBODIMENTS

Figure 1A:
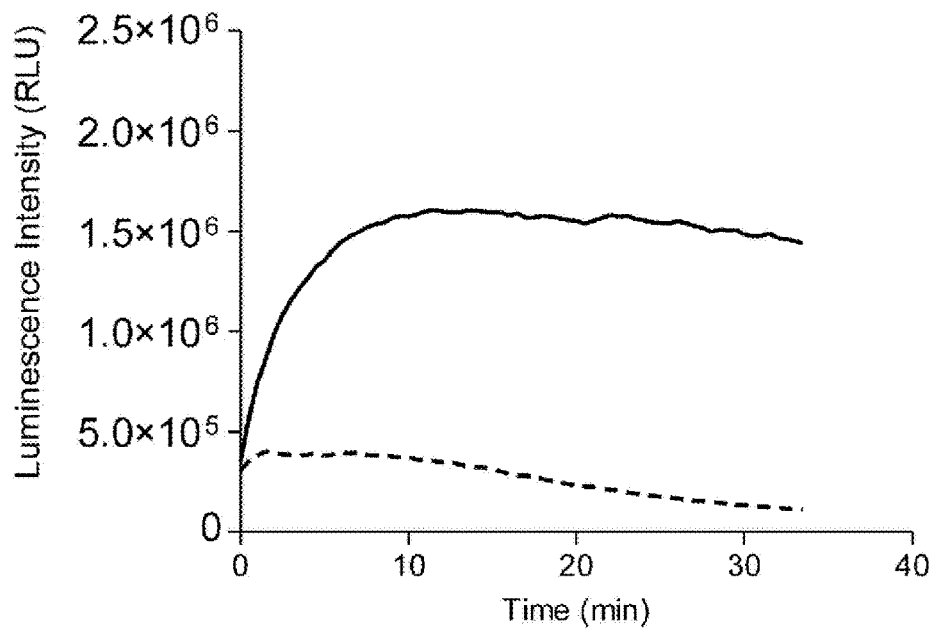
FIG. 1 depicts the reactivity of thrombin and plasmin on the S1 ($CH_3O$—$(CH_2CH_2O)_2$-acetyl-beta-Ala-Gly-Arg-aminoluciferin TFA salt) substrate (FIG. 1*a*) using 150 nM thrombin (solid line) and 40 nM plasmin (striped line) and the reactivity of thrombin and plasmin on the S2 (pyroGlu-Phe-Lys-aminoluciferin TFA salt) substrate (FIG. 1*b*) using 4 nM plasmin (striped line) and 15 nM thrombin (solid line) in Trsi buffered saline (TBS) buffer with the concentrations of luciferase, ATP, $MgCl_2$ and $CaCl_2$ as described above. These results indicate that the substrates are more susceptible for their respective enzyme.

In a first aspect, the present invention relates to a method for in vitro determining generation of a haemostasis factor in a test sample comprising determining the amount of said haemostasis factor generated using a chemiluminescent substrate specific for said haemostasis factor, wherein preferably a luminescent molecule is liberated by a haemostasis factor which is subsequently converted to produce a detectable light quant.

The present inventors have found that using such substrates, generation of haemostasis factor, e.g. thrombin generation and plasmin generation, can be measured continuously, semi-continuously or in a direct way without requiring calculation of the first derivative as is required for chromogenic or fluorogenic method for measuring generation of blood clotting factors, e.g., thrombin and/or fibrinolyic factors, e.g. plasmin. Typically, upon cleavage of a substrate of the invention by a haemostasis factor of interest, a 'luminescent molecule' is liberated which is prone to a subsequent chemical or enzymatic conversion that produces a detectable light signal (or "light quant"). Since the light quant is produced in an irreversible step, there is no accumulation of output signal. It is a significant advantage of the present method, as compared to existing methods employing fluorescent substrates, that a signal can be detected real-time that is directly proportional to the amount of the haemostasis factor present at any given time point; there is no need to calculate the first derivative of an accumulating optical signal. In the present method there is no interference with further production of light signals. In addition, no external light source and optical filters are required for measuring the signal. Thus, the method of the present invention is much more convenient than the prior art methods.

Altogether, the present invention provides an improved, sensitive method for monitoring generation of haemostasis factors in a test sample. The method of the present invention allows for the design of an optical point-of-care device for measuring the generation of one or more haemostasis factors.

The haemostasis factor may be any blood clotting factor and may be selected from the group of serine proteases, in particular serine endopeptidases (EC 3.4.21), preferably selected form the group consisting of thrombin, factor Xa, plasmin, factor VIIa, factor IXa, plasma kalikrein, factor XIIa, factor XIa, tissue plasminogen activator (tPA), preferably tc-tPA, activated Protein C, and urokinase (uPA) preferably tc-UPA. In an embodiment, the haemostasis factor is selected from thrombin and plasmin.

The generation of haemostasis factors may be detected using an amino-modified aminoluciferin, which modification comprises a substrate for the haemostasis factor that is generated. Suitable substrates for monitoring the coagulation reaction include derivatized peptides which are specifically cleaved by said haemostasis factor, e.g., blood clotting factor thrombin or fibrinolytic factor plasmin that is produced as a final event in the coagulation pathway or after fibrin formation. The peptides are linked to a chemiluminescent reporter molecule, such as aminoluciferin, still retaining the ability to be cleaved. The blood clotting factor, e.g. thrombin or plasmin, is able to recognize the peptide, cleave the cleavable linker, and a chemiluminescent reporter molecule, such as aminoluciferin, is formed that in the presence of ATP, luciferase and, optionally $Mg^{2+}$, typically results in light emission.

The method of the invention can be used to determine the effects of drugs, inhibitors, proteins, cells or other additives on generation of blood clotting factors such as thrombin or plasmin. In order to measure the effect of such additives they can be added to the reaction mixture. These additives may also be coated to the wells in the container in which the assay is performed, such as the wells of 96-well plates. When endothelial cells are part of the reaction mixture they may be cultured in the wells.

The luminescent signal may be measured by any method known in the art. Suitable detection methods comprise the use of a light detection apparatus, which includes, without limitation, a luminometer, a Charge-Coupled Device (CCD) camera, an X-ray film, and high-speed photographic film. Typically, said luminometer comprises a blue-sensitive photomultiplier tube (PMT), a red-sensitive photomultiplier tube (PMT), or other PMTs optimized for specific applications. Preferably, said light detection methods further include the use of an optical filtering device to block or reduce unwanted light emission either from the substrate or from the product. The detection methods may further include a method and/or a device for detecting or registering light in a sequential manner that eliminates or reduces unwanted signal from the substrate. Said luminescent signal is preferably measured continuously, semi-continuously or in a non-continuous fashion. The amount of haemostasis factor (for example, thrombin or plasmin) is directly proportional to the signal measured, such that there is no need to convert the measured signal into a first derivative. Hence, in a preferred embodiment, a method as defined herein before is provided, wherein determining the amount of said haemostasis factor generated, preferably thrombin and/or plasmin, by measuring a luminescent signal does not involve calculating the first derivative of said luminescent signal.

In an embodiment, the method of the invention comprises: providing a reaction mixture comprising a test sample to be tested, a trigger molecule for inducing generation of haemostasis factor, e.g. thrombin and/or plasmin, and a chemiluminescent substrate specific for said haemostasis factor, for example thrombin or plasmin; and determining the amount of said haemostasis factor, such as thrombin or plasmin, generated by measuring a luminescent signal, preferably using a luciferase, typically in the presence of ATP. Preferably the reaction mixture that is provided comprises $Mg^{2+}$.

The reaction mixture may comprise one or more coagulation initiators. A variety of suitable coagulation initiators may be employed. Such initiators trigger the coagulation pathways at the standard points that are commonly used for medical tests. For example, the extrinsic coagulation pathway initiator tissue factor will together with factor VII and calcium activate factor X either directly or indirectly via first the activation of factor IX. The intrinsic coagulation pathway initiator will activate factor XII to in turn activate factor XI. Suitable initiators of the extrinsic coagulation pathway are well known in the art and include tissue factor, and the like. Suitable initiators for the intrinsic coagulation pathway are also well known in the art and include ellagic acid, kaolin, silica, and the like. Description of these and other initiators are provided in *Laboratory Evaluation of Hemostasis and Thrombosis* (Third Edition), 1983, Marjorie S. Sirridge and Reaner Shannon, Lea & Febiger, Philadelphia; and *Hemostatis and Thrombosis, a conceptual approach* (Second Edition), 1983, Jack Hirsh and Elizabeth Brain, Churchill Livingstone, New York.

The reaction mixture suitably also contains structures having a phospholipid-containing surface. The phospholipid-containing surface suitably comprises negatively charged phospholipids, i.e. anionic phospholipids, such as phosphatidylserine. Suitable examples thereof include phospholipid vesicles, cephalin, cells, in particular (activated) endothelial cells, (activated) blood platelets, bacteria, viruses, matrices of (activated) endothelial cells or microvesicles or other suitable structures known to the person skilled in the art. The presence of such structures is particularly advantageous in embodiments relating to vitamin K dependent clotting factors. Such vitamin K dependent clotting factors bind to anionic phospholipid-containing surfaces via so-called GLA domains. The cofactors also typically bind to the surfaces. The presence of structures expressing anionic phospholipid-containing surfaces accelerates the reaction of vitamin K dependent clotting factors several orders of magnitude.

The reaction mixture may also include fibrin, a fibrin fragment or a fibrin generation substance. Fibrin is an important cofactor for plasmin generation induced by tPA. Thus in one embodiment, the reaction mixture comprises fibrin or a fragment of fibrin suitable to act as a cofactor for plasmin generation.

In an embodiment, the chemiluminescent substrate specific for said haemostasis factor comprises a peptide comprising a cleavage site specific for said haemostasis factor covalently linked to or otherwise coupled to preferably the amino group of aminoluciferin or to the carboxy-terminal modified derivative via a peptide bond. Preferably, the N-terminus of the substrate is modified to prevent degradation by aminopeptidases, e.g., using an amino-terminal protecting group; these are known to the person skilled in the art In case of the haemostasis factor being thrombin, the chemiluminescent thrombin substrate may comprise a peptide comprising a thrombin cleavage site coupled to aminoluciferin. In case of the haemostasis factor being plasmin, the chemiluminescent plasmin substrate may comprise a peptide comprising a plasmin cleavage site coupled to aminoluciferin.

In the absence of the appropriate haemostasis factor, a mixture comprising a substrate specific for a haemostasis factor will generate minimal light as minimal free aminoluciferin is present. In the presence of the appropriate haemostasis factor, the peptide bond linking the substrate and aminoluciferin can be cleaved by the haemostasis factor to yield aminoluciferin, a substrate for luciferase. Thus, in the presence of luciferase light is generated, which is proportional to the amount of haemostasis factor generated.

The chemiluminescent substrate specific for said haemostasis factor may be of the form B-X-Arg-NH-Y, X-Arg-NH-Y, B-X-Lys-NH-Y or X-Lys-NH-Y, where B is an amino-terminal protecting group, and X may be any amino acid sequence, dipeptide, tripeptide, or the like and may or may not include a spacer molecule; preferably, X is beta-Ala-Gly or pyroGlu-Phe. Suitable amino-terminal protecting groups include, without limitation, Fmoc (fluorenylmethyloxycarbonyl), Cbz (benzyloxycarbonyl), t-Boc (tert-butyloxycarbonyl), acetyl, $PEG_n$ and $PEG_n$-acetyl wherein n is in the range from 1-20, preferably in the range from 1-10, preferably in the range from 1-8, more preferably in the range from 1-5, most preferably n is 5 and their PEG (methyl)ether derivatives. Y is the chemiluminescent reporter molecule, linked to the peptide by a hydrolyzable amide bond. Typically Y will be converted by luciferase and thus produce a light quant only after the amide linkage has been hydrolyzed by said haemostasis factor, e.g., thrombin or plasmin. Prior to hydrolysis of the amide linkage, the reporter molecule cannot be converted. In a suitable embodiment, Y may be aminoluciferin.

Exemplary substrate peptides for thrombin include beta-Ala-Gly-Arg linked to aminoluciferin, $PEG_n$-acetyl-Gly-Gly-Arg linked to aminoluciferin, wherein n preferably is 1, 2, 3, 4 or 5, more preferably n is 3, and $PEG_n$-acetyl-beta-Ala-Gly-Arg linked to aminoluciferin, wherein n preferably is 1, 2, 3, 4 or 5, more preferably n=5. Preferably PEG is in the form of its methyl ether, thus $CH_3O(CH_2CH_2O)_n$. It should be noted that in the embodiments of the invention $PEG_n$ corresponds to $CH_3O(CH_2CH_2O)_{n-1}$; e.g. $PEG_3$ corresponds to $CH_3O(CH_2CH_2O)_2$. The latter two substrates ($PEG_n$-acetyl-Gly-Gly-Arg linked to aminoluciferin and $PEG_n$-acetyl-beta-Ala-Gly-Arg linked to aminoluciferin) are particularly suitable as they are soluble and are cleaved by thrombin. Substrates comprising beta-Ala-Gly-Arg linked to aminoluciferin are highly preferred since they have high specificity for thrombin and are not sensitive to e.g. plasmin. Substrates comprising Gly-Gly-Arg-aminoluciferin may be sensitive to e.g. plasmin, which may be present in plasma.

Exemplary substrate peptides for plasmin include Cbz-Phe-Arg-aminoluciferin, Ac-Phe-Arg-aminoluciferin, Phe-Arg-aminoluciferin, and $PEG_n$-acetyl-Phe-Arg-aminoluciferin, wherein n preferably is 1, 2, 3, 4 or 5, more preferably n is 5. Preferably PEG is in the form of its methyl ether, thus $CH_3O(CH_2CH_2O)_n$. Another preferred substrate is pyroGlu-Phe-Lys-aminoluciferin or the TFA salt thereof.

Other preferred substrates according to the invention are:
$CH_3O(CH_2CH_2O)_n$-acetyl-beta-Ala-Gly-Arg-aminoluciferin, wherein n is 0, 1, 2, 3 or 4, preferably 2 or 4, more preferably 4;
$CH_3O(CH_2CH_2O)_n$-acetyl-Gly-Gly-Arg-aminoluciferin, wherein n is 0, 1, 2, 3, or 4, preferably 2 or 4, more preferably 2;
a salt of the substrates here above, preferably the TFA salt.

The reaction mixture may further comprise a luciferase capable of converting aminoluciferin into amino-oxyluciferin, and ATP and preferably further comprises $Mg^{2+}$. The principle of chemiluminescence involving luciferase is well known by the skilled person. It typically uses luciferase, luciferin, ATP and oxygen for photon production. Luciferase catalyzes the conjugation of luciferin to ATP and the subsequent oxidation of the luciferyl-AMP intermediate. Ultimately, the luciferase provides an environment in which the oxidized luciferin intermediate rearranges to produce oxyluciferin and a single photon with high-quantum efficiency. Light intensity resulting from such luminescence is dependent on the concentrations of the components involved in the chemical or enzymatic conversion of the liberated luminescent molecule. By using an excess of such components, the luminescent signal of the method of the invention becomes dependent only on the generation of free luminescent molecules by cleavage of the substrate by the haemostasis factor of interest, e.g., thrombin or plasmin. Under such circumstances, the light intensity thus is proportional to the generation of said haemostasis factor, e.g., thrombin or plasmin generation.

The reaction may further comprise magnesium ions as it was found that these magnify the luminescent signal generated. However, it is also possible to achieve this effect with other divalent cations.

The luciferase may be any luciferase known in the art or yet to be discovered or engineered. Many luciferases are known in the art. They can be commercially obtained from manufacturers such as Promega, Sigma, and the like. The luciferase may be a native, a recombinant or a mutant luciferase. Said mutant luciferase may be a modified luciferase comprising one or more amino acid substitutions, amino acid deletions, or amino acid insertions, as long as it retains its luciferase activity, preferably at least 25%, 50%, 75% of the luciferase activity of the native (recombinant) luciferase. It may be derived from any organism, as long as it has luciferase activity.

The test sample may be any type of test sample known to the skilled person. The test sample may be selected from the group consisting of cells, physiological fluids, blood, urine, sputum, and the like. In a suitable embodiment, the test sample is selected from the group consisting of whole blood, drain fluid, platelet-rich plasma and platelet-poor plasma.

The trigger molecule for inducing generation of said blood clotting factor, such as thrombin, may be an initiator of the extrinsic pathway, in particular tissue factor, or of the intrinsic pathway, in particular selected from the group consisting of glass, kaolin silica and ellagic acid. The trigger molecule in vivo for inducing generation of blood clotting factors such as thrombin is suitably tissue factor (TF). TF mediates thrombin formation by complexing with factor VIIa to directly convert factor X to factor Xa (extrinsic pathway), or indirectly by generating factor Xa by converting factor IX to factor IXa, which, in turn, complexes with factor VIIIa to convert factor X to factor Xa. Factor Xa, once generated, complexes with its co-factor, V(a), to convert prothrombin (II) to thrombin (IIa). TF is preferred because it is the same trigger that is found in the body for the extrinsic pathway. Triggers for the intrinsic route are for example surfaces like glass, kaolin, silica, or ellagic acid.

In an embodiment, the method according to the invention comprises:
allowing factor Xa to convert prothrombin to thrombin;
allowing thrombin to convert the chemiluminescent thrombin substrate into peptide and aminoluciferin; and
allowing luciferase to convert aminoluciferin into amino-oxyluciferin upon production of a light quant.

In an embodiment, the method of the invention comprises: allowing an initiator of the extrinsic pathway to generate in the presence of factor VII(a) factor Xa or factor IXa, allowing factor IXa to generate factor Xa, allowing factor Xa to convert prothrombin to thrombin; allowing thrombin to convert the chemiluminescent thrombin substrate into peptide and aminoluciferin; and allowing luciferase to convert aminoluciferin into amino-oxyluciferin with the production of a light quant.

In an embodiment, the method of the invention comprises: allowing an initiator of the intrinsic pathway to generate factor XIIa, allowing factor XIIa to generate factor XIa, allowing factor XIa to generate factor IXa, allowing factor IXa to generate factor Xa, allowing factor Xa to convert prothrombin to thrombin; allowing thrombin to convert the chemiluminescent thrombin substrate into peptide and aminoluciferin; and allowing luciferase to convert aminoluciferin into amino-oxyluciferin with the production of a light quant.

The trigger molecule for inducing plasmin generation may be selected from the group consisting of urokinase, streptokinase, and tissue plasminogen activator, and is preferably tissue plasminogen activator. The trigger molecule can be naturally isolated or can be produced by recombinant methodology. Thus the group of trigger molecules also comprises recombinant urokinase, recombinant streptokinase and recombinant tissue plasminogen activator. Plasmin is formed by activation of the pro-enzyme, plasminogen, by plasminogen activators. Tissue plasminogen activators are found in many tissues. Tissue plasminogen activator is released by endothelial cells and activated platelets. The trigger molecule for inducing generation of plasmin in the assay of the invention is suitably tissue plasminogen activator (tPA) because it is also the trigger in the natural situation in the body. Examples of other triggers are urokinase and streptokinase.

In an embodiment, the method of the invention comprises: allowing urokinase, streptokinase or tPA to convert plasminogen to plasmin, optionally in the presence of fibrin or fibrin fragments; allowing plasmin to convert the chemiluminescent plasmin substrate into peptide and aminoluciferin; and allowing luciferase to convert aminoluciferin into amino-oxyluciferin upon production of a light quant.

In an embodiment, the method of the invention includes: i) conversion of prothrombin to thrombin by factor Xa; conversion of factor X to factor Xa by TF-Factor VIIa complex or factor IXa Factor-VIII(a) complex; conversion of factor VII to factor VIIa by TF-factor-VIIa complex; conversion of plasminogen to plasmin by tPA or uPA or streptokinase or with a lesser efficacy by the intrinsic factors factor XIIa, factor XIa and kallikrein; conversion of factor IX to factor IXa by TF-VIIa complex or by factor XIa; conversion of factor XI to factor XIa by factor XIIa or thrombin; conversion of factor XII to factor XIIa by prekallikrein or factor XIIa; conversion of prekallikrein to kallikrein by glas, kaolin, silica or ellagic acid; conversion of protein C to activated protein C by thrombin-thrombomodulin complex; conversion of thrombin activatable fibrinolysis inhibitor to activated thrombin activatable fibrinolysis inhibitor, by thrombin or complex of thrombin-thrombomodulin; conversion of single chain-tPA (sc-tPA) to two chain tPA (tc-tPA) by plasmin or with lesser efficacy by factor Xa and kallikrein; conversion of single chain-uPA to two chain uPA by plasmin or with lesser efficacy by factor XIIa and kallikrein; ii) conversion of a substrate specific for the haemostasis factor generated to aminoluciferin by thrombin or plasmin formed in i); and iii) conversion of aminoluciferin to amino-oxyluciferin by luciferase upon which a single photon with high-quantum efficiency is produced (Cosby et al. 2007. Cell notes. Issue 18:9-11). By keeping the concentrations of all components in the reaction constant, except for the haemostasis factor concerned, light intensity is proportional to the concentration of said haemostasis factor.

The chemiluminescent substrates described in the first aspect of the invention are in a further aspect of the invention provided as such.

In a further aspect, the present invention is concerned with a kit for in vitro determining generation of a haemostasis factor, preferably thrombin and/or plasmin, in a test sample, comprising a first container holding a chemiluminescent substrate specific for said haemostasis factor, and one, two, three or more additional containers each holding a distinct reagent selected from the group consisting of luciferase, ATP, an $Mg^{2+}$ source and a trigger molecule for inducing generation of said haemostasis factor, wherein the chemiluminescent substrate is preferably a chemiluminescent substrate according to the invention.

The trigger molecule for generation of said blood clotting factor, e.g., thrombin and/or plasmin generation, may be an initiator of the extrinsic pathway, in particular tissue factor (TF) or an initiator of the intrinsic pathway, in particular glass, kaolin and ellagic acid.

The chemiluminescent substrate specific for said haemostasis factor, preferably thrombin and/or plasmin, may be as defined hereinabove.

In a further aspect, the present invention is concerned with a kit for in vitro determining thrombin generation in a test sample, comprising a first container holding a chemiluminescent thrombin substrate, preferably a chemiluminescent thrombin substrate according to the invention, and one, two, three or more additional containers, each holding a distinct reagent selected from the group consisting of luciferase, ATP, an $Mg^{2+}$ source and a trigger molecule for inducing thrombin generation.

In another aspect, the present invention pertains to a kit for in vitro determining plasmin generation in a test sample, comprising a first container holding a chemiluminescent plasmin substrate, preferably a chemiluminescent plasmin substrate according to the invention, and one, two, three or more additional containers each container comprising a distinct reagent selected from the group consisting of luciferase, ATP, an $Mg^{2+}$ source and a trigger molecule for inducing plasmin generation.

The trigger molecule for inducing plasmin generation may be selected from the group consisting of urokinase, streptokinase, and tissue plasminogen activator (tPA).

The kit may further comprise an anionic-phospholipid containing surface and/or a fibrin, a fibrin fragment or a fibrin generating substance.

The kit may also further comprise a container holding one or more coagulation initiators as described above.

In this document and in its claims, the verb "to comprise" and its conjugations is used in its non-limiting sense to mean that items following the word are included, but items not specifically mentioned are not excluded. In addition, the verb "to consist" may be replaced by "to consist essentially of" meaning that a composition of the invention may comprise additional component(s) than the ones specifically identified, said additional component(s) not altering the unique characteristics of the invention.

In addition, reference to an element by the indefinite article "a" or "an" does not exclude the possibility that more than one of the element is present, unless the context clearly requires that there be one and only one of the elements. The indefinite article "a" or "an" thus usually means "at least one".

All patent and literature references cited in the present specification are hereby incorporated by reference in their entirety.

It will be clear that the above description is included to illustrate some embodiments of the invention, and not to limit the scope of protection. Starting from this disclosure, many more embodiments will be evident to a skilled person which are within the scope of protection and the essence of this invention and which are obvious combinations of prior art techniques and the disclosure of this patent.

EXAMPLES

Example 1: Features of Two Typical Substrates

The Chemiluminescent Assay for Measuring Thrombin Generation in Plasma

In a 96-wells plate (final volume 120 μl), the following components were added:
80 μl Normal pooled plasma (NPP),
2 μl Cephalin (Roche product number 524298; dissolved in 1 ml distilled water)
2 μl Tissue Factor (Innovin, Siemens Healthcare Diagnostics 500× diluted),
10 μl MeO—(CH$_2$CH$_2$O)$_2$-acetyl-beta-Ala-Gly-Arg-aminoluciferin TFA salt (thrombin specific substrate (10 mM)), or pyroGlu-Phe-Lys-aminoluciferin TFA salt (plasmin specific substrate (10 mM))
2 μl recombinant-tPA (Actilyse®, Boehringer Ingelheim, 193 IU/ml),
2 μl Luciferase (Sigma, 72 μg/ml),
2 μl ATP (Sigma, 0.33 mM),
2 μl MgCl$_2$ (8.3 mM)
14 μl TRIS/NaCl buffer (50 mM TRIS and 150 mM NaCl, pH 7.4).

This reaction mixture was mixed, followed by the addition of 4 μl TRIS/NaCl buffer with Ca$^{2+}$ to start thrombin generation. Final concentration 16.7 mM. The resultant was mixed rapidly, and thrombin generation was monitored in a Fluostar. The settings of the Fluostar were: 140 cycli of 30 seconds, Gain: Maximum=4095. Prior to measurement, 25 μl reaction mixture was taken from the well having a total volume of 120 μl. This was pipetted in a 384-well multi-titre plate suitable for measuring luminescence. The measurement was started immediately. Luminescence is depicted in Relative luminescence units (RLU).

Substrates:

The substrates used for testing this luminescence assay were a thrombin specific substrate (S1: MeO—(CH$_2$CH$_2$O)$_2$-acetyl-beta-Ala-Gly-Arg-aminoluciferin TFA salt) and a plasmin specific substrate (S2: pyroGlu-Phe-Lys-aminoluciferin TFA salt)

Experiments

Reactivity of S1 and S2 was determined in buffer and plasma. Measurements were performed under the assay conditions as stated above unless indicated otherwise by individual experiments.

Figure 1B:
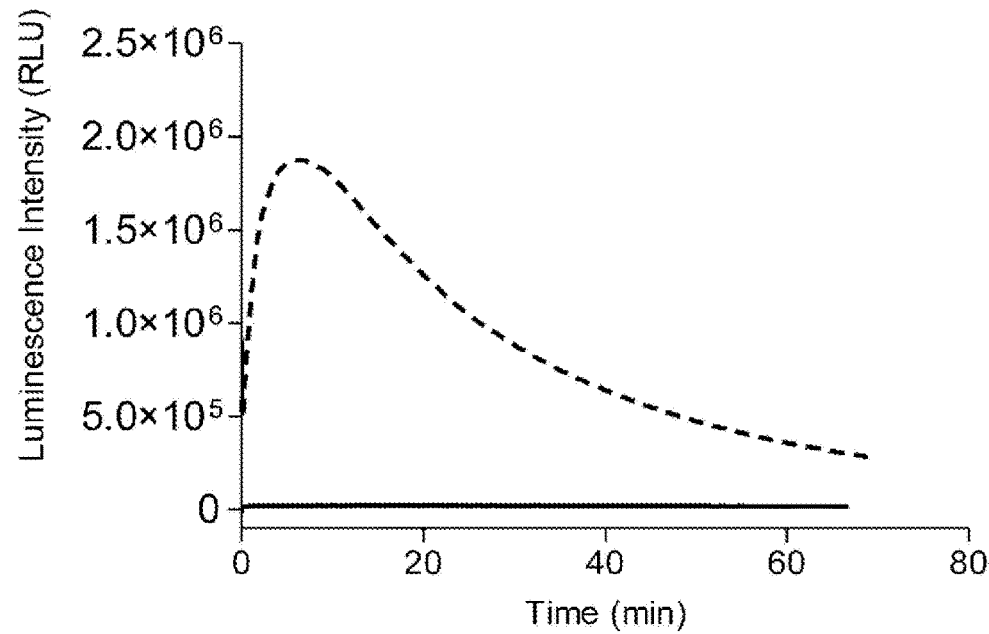

Results:

FIG. 1 demonstrates the reactivity of thrombin and plasmin on the S1 substrate (FIG. 1a) using 150 nM thrombin (solid) and 40 nM plasmin (striped) and the reactivity of thrombin and plasmin on the S2 substrate (FIG. 1b) using 4 nM plasmin (striped) and 15 nM thrombin (solid) in TBS buffer with the concentrations of luciferase, ATP, MgCl$_2$ and CaCl$_2$ as described above. These results indicate that the substrates are more susceptible for their respective enzyme.

Figure 2A:
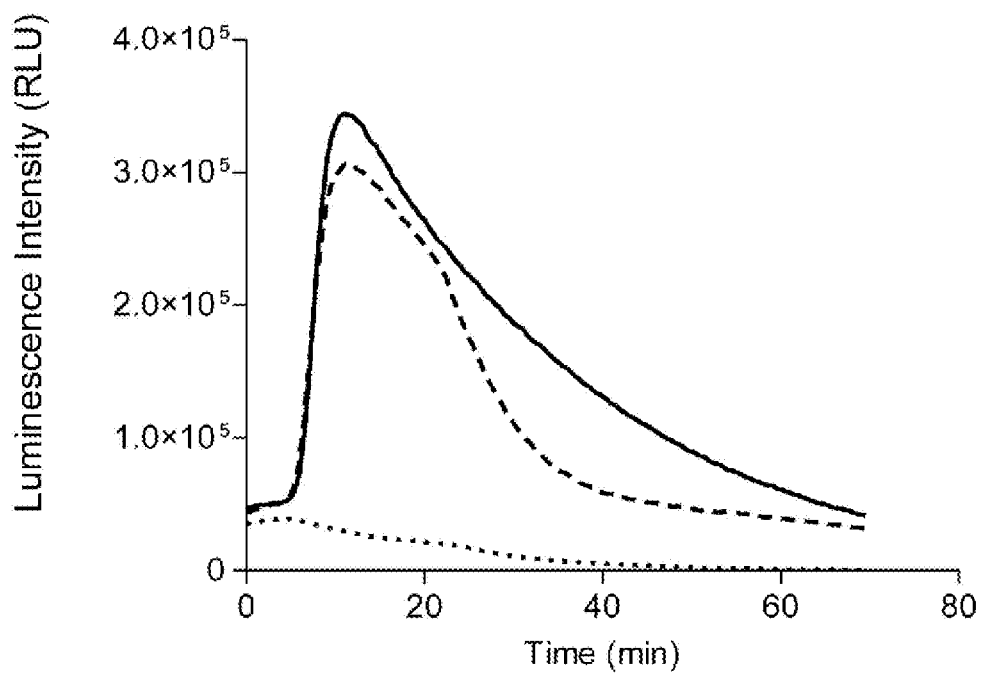
FIG. 2 depicts the luminescence intensity of thrombin substrate S1 (FIG. 2*a*) or the plasmin substrate S2 (FIG. 2*b*) in normal pooled plasma without tPA (solid), with tPA (striped) and in FVIII deficient plasma incubated with tPA (dotted).
Figure 2B:
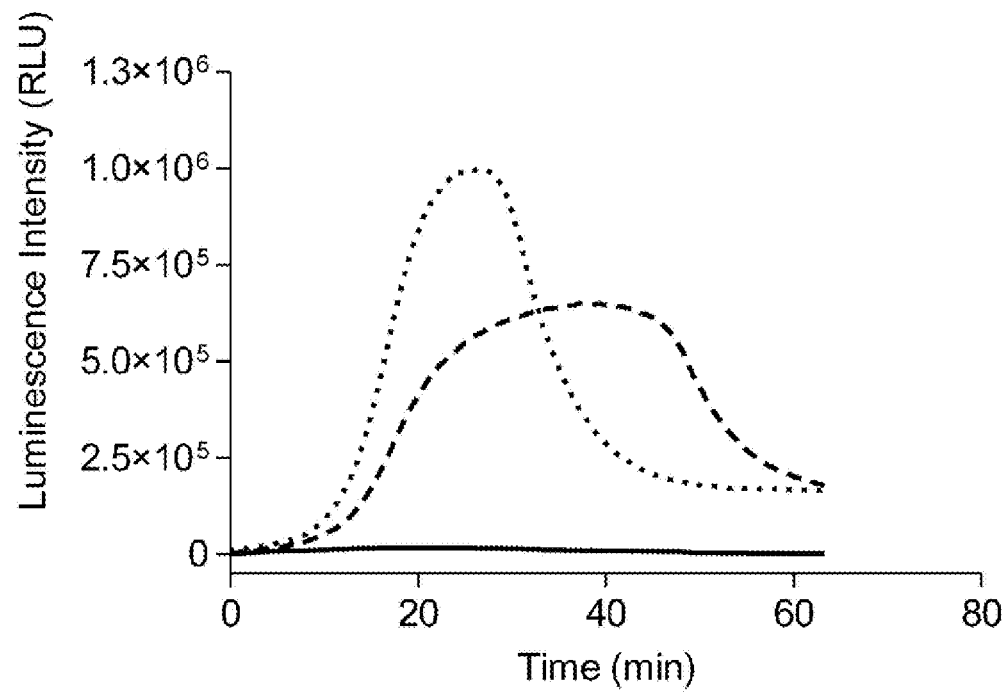

FIG. 2 demonstrates the luminescence intensity of thrombin substrate S1 (FIG. 2a) or the plasmin substrate S2 (FIG. 2b) in normal pooled plasma without tPA (solid), with tPA (striped) and in FVIII deficient plasma incubated with tPA (dotted).

Figure 3A:
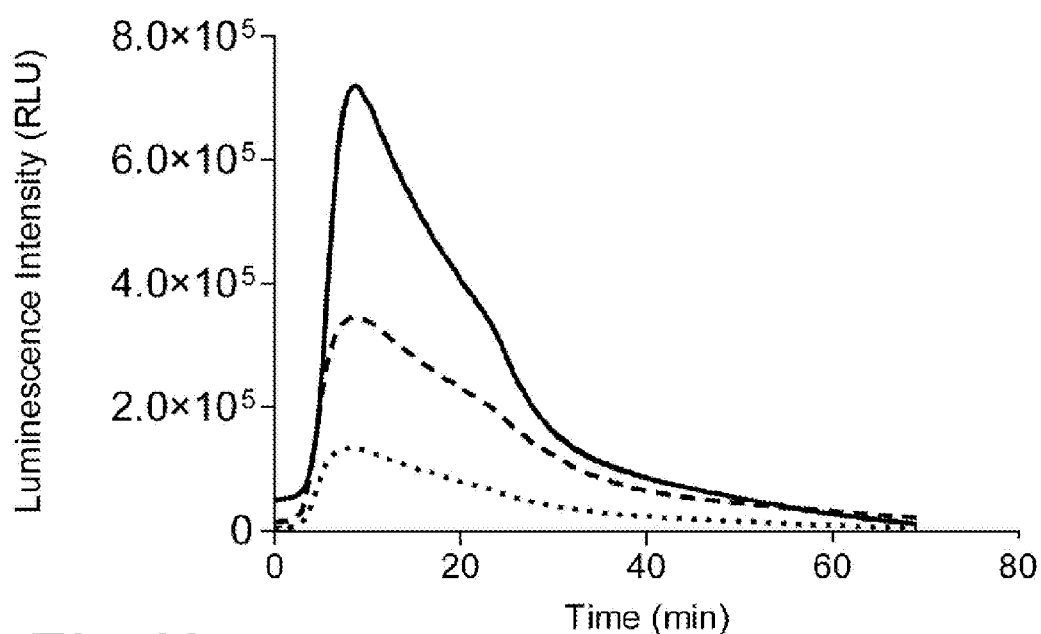
FIG. 3 depicts the effect of magnesium on the conversion of S1 (FIGS. 3*a*) and S2 (FIG. 3*b*) in a regular assay with normal pool plasma with a final concentration of 8.3 mM (solid), 0.83 mM (striped) and no (dotted) magnesium.
Figure 3B:
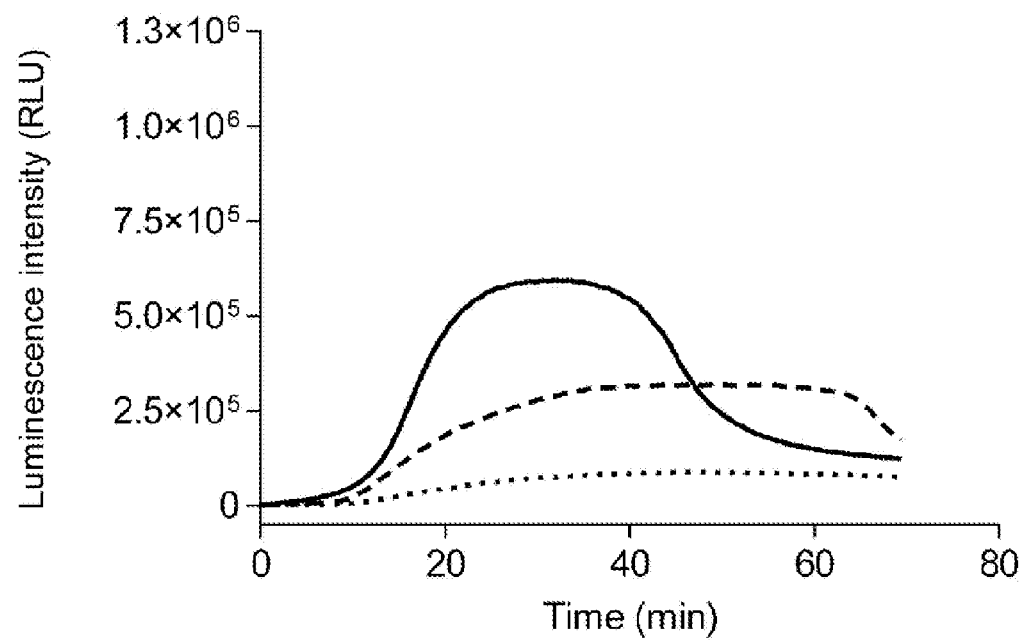

FIG. 3 demonstrates the effect of magnesium on the conversion of S1 (FIG. 3a) and S2 (FIG. 3b) in a regular assay with normal pool plasma with a final concentration of 8.3 mM (solid), 0.83 mM (striped) and no (dotted) magnesium.

Example 2: Various Substrates Tested with Plasmin and Thrombin

Various substrates were analyzed using thrombin and plasmin. The assay was essentially performed as described in example 1. However, instead of plasma, plasmin or thrombin were added to final concentrations of 30 nM (thrombin) or 40 nM (plasmin).

In Table 1 results are depicted for the various substrates. As can be clearly observed, plasmin and thrombin induce specific luminescence signals.

| Substrate | RLU thrombin | RLU plasmin | RLU thrombin/ RLU plasmin |
|---|---|---|---|
| CH$_3$O—(CH$_2$CH$_2$O)$_2$-acetyl-Phe-Arg-aminoluciferine•TFA | 300946 | 759874 | 0.40 |
| CH$_3$O—(CH$_2$CH$_2$O)$_4$-acetyl-Phe-Arg-aminoluciferine•TFA | 340768 | 1282351 | 0.27 |
| PyroGlu-Phe-Lys-aminoluciferine•TFA | 139546 | 1999875 | 0.07 |
| H-beta-Ala-Gly-Arg-aminoluciferine•2TFA | 292161 | 62387 | 4.7 |
| Cbz-Gly-Gly-Arg-aminoluciferine•TFA* | 771302 | 146486 | 5.3 |
| CH$_3$O—(CH$_2$CH$_2$O)$_2$-acetyl-beta-Ala-Gly-Arg-aminoluciferine•TFA | 814171 | 251299 | 3.2 |
| CH$_3$O-acetyl-beta-Ala-Gly-Arg-aminoluciferine•TFA | 925567 | 294631 | 3.1 |
| CH$_3$O—(CH$_2$CH$_2$O)$_4$-acetyl-beta-Ala-Gly-Arg-aminoluciferine•TFA | 293198 | 134983 | 2.2 |

*very low solubility in buffer +10% DMSO; not soluble in buffer without DMSO

The invention claimed is:

1. A chemiluminescent substrate selected from the group consisting of:
   PEGn-acetyl-X-Lys-NH-Y and PEGn-acetyl-X-Arg-NH-Y, or a salt of thereof, wherein n is an integer in the range of 1-5, wherein Y is a chemiluminescent reporter moiety linked to the Lys or Arg by a hydrolyzable amide bond, and wherein X is an amino acid sequence;
   PEGn-acetyl-Phe-Arg-aminoluciferin, wherein n is an integer in the range of 1-5;
   CH$_3$O(CH$_2$CH$_2$O)n-acetyl-beta-Ala-Gly-Arg-aminoluciferin, wherein n is 1, 2, 3 or 4;
   CH$_3$O(CH$_2$CH$_2$O)n-acetyl-Gly-Gly-Arg-aminoluciferin, wherein n is 1, 2, 3 or 4;
   or a salt thereof.

2. A chemiluminescent substrate according to claim 1, wherein said chemiluminescent substrate is CH$_3$O(CH$_2$CH$_2$O)$_n$-acetyl-beta-Ala-Gly-Arg-aminoluciferin, wherein n is 2 or 4.

3. A chemiluminescent substrate according to claim 2, wherein n is 4.

4. A chemiluminescent substrate according to claim 1, wherein said chemiluminescent substrate is CH$_3$O(CH$_2$CH$_2$O)$_n$-acetyl-Gly-Gly-Arg-aminoluciferin, wherein n is 2 or 4.

5. A chemiluminescent substrate according to claim 4, wherein n is 2.

6. A chemiluminescent substrate according to claim 1, wherein said chemiluminescent substrate is a TFA salt.

7. A chemiluminescent substrate according to claim 1, wherein NH-Y is aminoluciferin.

8. A kit for in vitro determining generation of a blood hemostasis in a test sample, comprising a first container holding a chemiluminescent substrate selected from claim 1 and one or more additional containers each holding a distinct reagent selected from the group consisting of luciferase, ATP, an $Mg^{2+}$ source and a trigger molecule for inducing generation of said blood hemostasis factor.

9. A method for in vitro determining the generation of a blood hemostasis factor in a test sample comprising:
  contacting a test sample with a trigger molecule for inducing the generation of said blood hemostasis factor in the test sample, a chemiluminescent substrate selected from claim 1 which contains a cleavage site specific for said blood haemostasis factor to obtain a reaction mixture;
  measuring a luminescent signal which indicates that said blood hemostasis factor has cleaved the chemiluminescent substrate to release the aminoluciferin reporter moiety from the substrate; and
  determining the amount of said blood hemostasis factor based on the measurement of the luminescent signal.

10. The method according to claim 9, wherein the haemostasis factor is selected from the group consisting of thrombin, plasmin, factor Xa, factor IXa, factor VIIa, factor XIa factor XIIa, kallikrein, activated Protein C, tc-tPA and tc-uPA.

11. The method according to claim 9, wherein the chemiluminescent moiety comprises aminoluciferin and the reaction mixture further comprises a luciferase capable of converting the aminoluciferin into aminooxyluciferin, ATP and $Mg^{2+}$.

12. The method according to claim 9, wherein the test sample is selected from the group consisting of whole blood, drain fluid, platelet-rich plasma and platelet-poor plasma.

13. The method according to claim 9, wherein the trigger molecule induces thrombin generation and the trigger molecule is an initiator of the extrinsic pathway, or the trigger molecule is an initiator of the intrinsic pathway selected from the group consisting of glass, kaolin, silica and ellagic acid.

14. The method of claim 13, wherein the initiator of the extrinsic pathway is tissue factor.

15. The method according to claim 9, wherein the blood hemostasis factor is plasmin and the trigger molecule for inducing plasmin generation is selected from the group consisting of urokinase, streptokinase, and tissue plasminogen activator.

16. The method according to claim 9, wherein said chemiluminescent substrate is $CH_3O(CH_2CH_2O)_n$-acetyl-beta-Ala-Gly-Arg-aminoluciferin, wherein n is 2 or 4.

17. The method according to claim 16, wherein n is 4.

18. The method according to claim 9, wherein said chemiluminescent substrate is $CH_3O(CH_2CH_2O)_n$-acetyl-Gly-Gly-Arg-aminoluciferin, wherein n is 2 or 4.

19. The method according to claim 18, wherein n is 2.

20. The method according to claim 9, wherein said chemiluminescent substrate is a TFA salt.

* * * * *